United States Patent
Geist et al.

(10) Patent No.: US 12,285,200 B2
(45) Date of Patent: Apr. 29, 2025

(54) LENGTH ADJUSTABLE MODULAR SCREW SYSTEM

(71) Applicant: INTEGRITY IMPLANTS INC., Palm Beach Gardens, FL (US)

(72) Inventors: Wyatt Drake Geist, Davie, FL (US); John Souza, Sr., Monroe, NC (US)

(73) Assignee: INTEGRITY IMPLANTS INC., Palm Beach Gardens, FL (US)

( * ) Notice: Subject to any disclaimer, the term of this patent is extended or adjusted under 35 U.S.C. 154(b) by 0 days.

(21) Appl. No.: 18/133,005

(22) Filed: Apr. 11, 2023

(65) Prior Publication Data
US 2023/0355286 A1 Nov. 9, 2023

Related U.S. Application Data

(60) Division of application No. 16/818,924, filed on Mar. 13, 2020, now Pat. No. 11,633,220, which is a (Continued)

(51) Int. Cl.
*A61B 17/86* (2006.01)
*A61B 17/70* (2006.01)
*A61B 17/56* (2006.01)

(52) U.S. Cl.
CPC ...... *A61B 17/8685* (2013.01); *A61B 17/7002* (2013.01); *A61B 17/7032* (2013.01); (Continued)

(58) Field of Classification Search
CPC ............ A61B 17/8625; A61B 17/8605; A61B 17/8685; A61B 17/7035; A61B 17/7037
See application file for complete search history.

(56) References Cited

U.S. PATENT DOCUMENTS 5,209,753 A 5/1993 Biedermann et al.
6,086,589 A 7/2000 Kuslich et al.
(Continued)

FOREIGN PATENT DOCUMENTS

EP 0841876 B1 5/1998
EP 1545355 B1 6/2006
(Continued)

OTHER PUBLICATIONS

Rasoulinejad, Parham, "Design and Development of a Novel Expanding Pedicle Screw for Use in the Osteoporotic Lumbar Spine" (2013) Electronic Thesis and Dissertation Repository. Paper 1614.
(Continued)

*Primary Examiner* — Olivia C Chang
(74) *Attorney, Agent, or Firm* — McNees Wallace & Nurick LLC

(57) ABSTRACT

A length adjustable modular screw includes a neck assembly and a shank. The neck assembly has proximal and distal ends and includes an expander component and a collet component that are slidably engagable by insertion of the expander component in a through channel of the collet component along a common axis. The length adjustable modular screw also includes a shank suitable for insertion and retention within a bone, the shank including a threaded portion between proximal and distal ends and a socket adapted to coaxially receive at least a portion of the distal end of the neck assembly. The length adjustable modular screw has a length that is selected by splaying at least a portion of the distal end of the engaged expander and collet components of the neck assembly within the socket of the shank.

14 Claims, 7 Drawing Sheets

Related U.S. Application Data continuation of application No. 16/018,942, filed on Jun. 26, 2018, now Pat. No. 10,758,285, which is a continuation-in-part of application No. PCT/US2017/048480, filed on Aug. 24, 2017.

(60) Provisional application No. 62/379,111, filed on Aug. 24, 2016.

(52) U.S. Cl.
CPC ...... *A61B 17/7035* (2013.01); *A61B 17/7037* (2013.01); *A61B 17/7082* (2013.01); *A61B 17/8625* (2013.01); *A61B 17/863* (2013.01); *A61B 17/8695* (2013.01); *A61B 2017/564* (2013.01); *A61B 2017/8655* (2013.01)

(56) References Cited

U.S. PATENT DOCUMENTS

| | | |
|---|---|---|
| 6,626,911 B1 | 9/2003 | Engman et al. |
| 6,778,861 B1 | 8/2004 | Liebrecht et al. |
| 7,186,255 B2 | 3/2007 | Baynham et al. |
| 7,306,603 B2 | 12/2007 | Boehm, Jr. et al. |
| 7,468,064 B2 | 12/2008 | Bruneau et al. |
| 7,588,593 B2 | 9/2009 | Aferzon |
| 7,875,065 B2 | 1/2011 | Jackson |
| 7,892,257 B2 | 2/2011 | Abdelgany |
| 7,967,850 B2 | 6/2011 | Jackson |
| 7,988,694 B2 | 8/2011 | Barrus et al. |
| 8,052,720 B2 | 11/2011 | Kuester et al. |
| 8,092,494 B2 | 1/2012 | Butler et al. |
| 8,162,991 B2 | 4/2012 | Strauss et al. |
| 8,202,304 B2 | 6/2012 | Boehm, Jr. et al. |
| 8,361,122 B2 | 1/2013 | Barrus et al. |
| 8,377,101 B2 | 2/2013 | Barrus et al. |
| 8,382,802 B2 | 2/2013 | Boehm, Jr. et al. |
| 8,623,061 B2 | 1/2014 | Quevedo et al. |
| 8,790,374 B2 | 7/2014 | Tott et al. |
| 8,852,239 B2 | 10/2014 | Jackson et al. |
| 10,117,679 B2 | 11/2018 | Biyani et al. |
| 2004/0147929 A1 | 7/2004 | Biedermann et al. |
| 2005/0055026 A1 | 3/2005 | Biedermann et al. |
| 2005/0273101 A1 | 12/2005 | Schumacher |
| 2006/0241593 A1 | 10/2006 | Sherman et al. |
| 2007/0233062 A1 | 10/2007 | Berry |
| 2007/0270855 A1 | 11/2007 | Partin |
| 2008/0147129 A1 | 6/2008 | Biedermann et al. |
| 2008/0161863 A1 | 7/2008 | Arnold et al. |
| 2008/0312701 A1 | 12/2008 | Butters et al. |
| 2009/0036929 A1 | 2/2009 | Reglos et al. |
| 2009/0062868 A1 | 3/2009 | Casutt |
| 2009/0157123 A1 | 6/2009 | Appenzeller et al. |
| 2010/0114108 A1 | 5/2010 | Strauss |
| 2010/0249846 A1 | 9/2010 | Simonson |
| 2011/0230915 A1 | 9/2011 | Anderson et al. |
| 2011/0307013 A1 | 12/2011 | Winslow et al. |
| 2011/0319946 A1 | 12/2011 | Levy et al. |
| 2012/0016423 A1 | 1/2012 | Hua |
| 2012/0041490 A1 | 2/2012 | Jacob et al. |
| 2012/0203288 A1 | 8/2012 | Lange et al. |
| 2012/0215264 A1 | 8/2012 | Lee |
| 2012/0271353 A1 | 10/2012 | Barry |
| 2012/0316609 A1 | 12/2012 | Wall et al. |
| 2013/0144342 A1 | 6/2013 | Strauss et al. |
| 2013/0172937 A1 | 7/2013 | Davenport et al. |
| 2014/0094860 A1 | 4/2014 | Reimels |
| 2014/0277187 A1 | 9/2014 | Fang et al. |
| 2014/0288605 A1 | 9/2014 | Mesiwala et al. |
| 2014/0336709 A1 | 11/2014 | Avidano et al. |
| 2014/0358182 A1 | 12/2014 | Puekert |
| 2015/0100093 A1 | 4/2015 | Harper |
| 2016/0270826 A1 | 9/2016 | Marino et al. |
| 2017/0112555 A1 | 4/2017 | Wallenstein et al. |
| 2019/0125410 A1 | 5/2019 | Harwell |
| 2019/0133660 A1 | 5/2019 | Lindner |
| 2019/0159820 A1 | 5/2019 | Geist et al. |
| 2020/0030006 A1 | 1/2020 | Errico et al. |

FOREIGN PATENT DOCUMENTS

| | | |
|---|---|---|
| RU | 2189200 C2 | 9/2002 |
| RU | 2003133987 C2 | 10/2007 |
| WO | 2005044117 | 5/2005 |
| WO | 2009079329 A2 | 6/2009 |
| WO | 2016054951 | 4/2016 |

OTHER PUBLICATIONS

International Search Report and Written Opinion from corresponding International Application PCT/US2017/048480 Nov. 7, 2017.

International Search Report and Written Opinion from corresponding International Application PCT/US2019/039026 dated Sep. 19, 2019.

Partial Supplementary European Search Report issued for Application No. / Patent No. 17844441.0—132 / 3503827 PCT/US2017/048480 dated Mar. 30, 2020.

LENGTH ADJUSTABLE MODULAR SCREW SYSTEM

PRIORITY

The present application is a U.S. Patent Application which is a divisional of and claims priority to U.S. patent application Ser. No. 16/818,924 filed on Mar. 13, 2020 titled "LENGTH ADJUSTABLE MODULAR SCREW SYSTEM", which is a continuation of and claims priority to U.S. patent application Ser. No. 16/018,942 filed Jun. 26, 2018 titled "LENGTH ADJUSTABLE MODULAR SCREW SYSTEM", which is a continuation in part of and claims priority to Patent Cooperation Treaty Patent Application PCT/US2017/048480 filed Aug. 24, 2017 titled "ADJUSTABLE BONE FIXATION SYSTEMS", which claims priority to and the benefit of U.S. Provisional Patent Application No. 62/379,111 filed Aug. 24, 2016 titled "ADJUSTABLE BONE FIXATION SYSTEMS", each of which is hereby incorporated by reference in its entirety.

FIELD OF INVENTION

The present invention relates to modular and adjustable assemblies for achieving alignment and fixation of two or more bones or bone segments. In particular embodiments, the invention relates to modular and adjustable assemblies for achieving fixation of bones in the spine.

BACKGROUND

The human skeleton is formed of bones, each bone performing a structural role, either individually or collectively with other bones. For example, the spine, which surrounds and protects the spinal cord and associated nerves, provides structure to the body, and enables fluid movement in many planes. Constructed of essentially twenty-four stacked vertebrae, the spine includes seven cervical vertebrae, twelve thoracic vertebrae and five lumbar vertebrae. A healthy spine is flexible in multiple directions to enable a broad range of physical movement. Intervertebral disks are disposed between adjacent vertebrae and provide cushioning and dampening to protect the spinal column and nerves in response to the various translational and rotational forces associated with body motion. Maintenance of the structural integrity and approximate axial alignment of the vertebrae is one key to good health.

A clinical subject's spine may be damaged or otherwise compromised in one of many ways. Abnormalities of or damage to the spine include but are not limited to scoliosis (abnormal lateral curvature), kyphosis, excessive lordosis, spondylolisthesis, displaced, degenerative or ruptured discs, fractures to one or more vertebral bodies and tumors. These and other possible spinal conditions directly and adversely affect mobility, and also cause moderate to extreme or even debilitating pain, at times accompanied by diminished or lost nerve function.

To ameliorate pain and restore loss of function associated with spinal conditions, a variety of conventional procedures have been developed using an array of mechanical surgical systems and implants that can secure two or more vertebrae in a relatively fixed position and can stabilize and straighten spinal deviations along the spinal axis. A stabilization system can be used without fusion treatment of the spine, or in conjunction with fusion treatment of the spine wherein one or more spacing devices is used to replace all or a portion of a vertebral disc. Typically, such discal implants are used together with natural bone components obtained from the clinical subject or a donor source, artificial bone, other biologic components to promote bone growth and fusion between the adjacent vertebral bodies. One or more such replacements may be accomplished in a spinal fixation surgery. The fixation system, with or without fusion components, operates to create a substantially rigid construct of bone and mechanical hardware that replaces damaged or diseased vertebrae and connects them to relatively healthier adjacent vertebrae.

Generally, spinal fixation systems involve some mode of stabilization using one or more rigid or substantially rigid surgical stabilization elements, such as a rod or a plate, and means for fastening and securing the stabilization element to bone. Fastening means can include one or more bone anchors, such as screws or bolts, assembled with connectors that enable engagement with one or more stabilization elements. The connectors may include hooks, clamps, cross connectors and other structures that engage with one or more of stabilization elements and anchors. These systems of anchor and connector assemblies and stabilization elements are secured to two or more vertebrae and are interconnected to provide support, encourage alignment or realignment of the vertebrae, and to achieve immobilization and fusion.

When spinal fixation surgery is performed from the anterior aspect of the clinical subject, it is conventional practice to affix a stabilization element in the form of a thin plate, typically formed of metal, to adjacent vertebral bodies and secure the plate using anchors, such as screws. When the fixation surgery is performed from the posterior aspect of the clinical subject, it is conventional practice to affix bone anchors into the vertebral bodies, typically in the pedicle. Multiple levels of adjacent vertebrae may be fixed in this manner. Interconnection of the secured anchors to the stabilization element creates a rigid fixation between the adjacent vertebral bodies.

The mode of surgical access may be open, that is, involving a relatively extensive resection of the soft tissue to plainly expose the vertebrae to be fixated. In some examples, the mode of surgical access may be minimal, wherein less invasive surgical techniques are used to minimize tissue resection. These less invasive approaches have many benefits to the clinical subject, however, the associated reduction in direct access and visualization of the vertebral tissue practically means that the anchor implants are difficult to access, grasp and manipulate with instruments, thus complicating the surgeon's efforts and often prolonging the amount of time that the clinical subject is in surgery.

Among the many challenges associated with placement of vertebral stabilization systems is the fact that adjacent vertebrae are typically not perfectly aligned. Indeed, along any particular portion of a spine, a series of adjacent vertebrae can deviate laterally a great deal from the central axis of the spine. Further, as a result of natural spinal curvature and any vertebral defects, corresponding portions, such as pedicles, of adjacent vertebra are not in the same plane. In the context of implanting spinal fixation systems, these variations can be accommodated to some extent by introducing bends or curves in the substantially rigid stabilization element(s) used for fixation. But in instances where the therapeutic benefit is obtained by realigning adjacent vertebrae, adjustment of the curvature of the stabilization element(s) is not a completely satisfactory solution. Accordingly, it is typically the case that the surgeon and surgical team must manipulate the spine and the system instruments in an attempt to align the secured anchors for attachment to a stabilization element. Often, the extent of nonalignment, both in terms of longitudinal and vertical planar positions of vertebrae along the spine, can cause failure of one or more of the system components, extend surgery, cause damage to the clinical subject's spine, and ultimately lead to a less than desirable clinical outcome. The challenges of access in minimally invasive procedures can compound the difficulties associated with non-aligned vertebral bodies.

Attempts have been made in the design of spinal fixation systems to address variability of spinal anatomy, such as those variations described above. In many examples of conventional systems, anchors are adapted to achieve a range of variability in positioning based on pivotal rotation of the anchor such that the axis of the secured anchor relative to the stabilization element can be varied. These are referred to as poly-axial and uni-axial anchors. They are useful in particular for facilitating attachment of a stabilization element to two or more vertebrae that are not aligned along the spinal axis. There are other examples of systems that are adapted with features that facilitate engagement of non-axially aligned vertebrae. But there are no conventional systems suitable for accommodating the variability in the relative height of adjacent vertebrae, wherein corresponding portions of adjacent vertebrae are not on the same plane. Further, there are no conventional systems that allow the surgeon the option to install bone anchors into the bone and then select from a suite of modular anchor components to achieve an optimized system for fixation that avoids or minimizes the problems associated with anatomical variations in the spine. Beyond the spine, such as for other bones and bone fragments in the body, there are likewise no systems that provide either or both modularity and length adjustability options in the fixation or reduction of bones and bone fragments.

To address the above-described challenges, there is need for bone anchors and other implants that meet or exceed the functionality of conventional anchors while also providing adjustability, and ideally, modularity, to address the height variability of vertebral bodies that do not share a common plane. Thus, what is needed, for example in the context of the spine, is a fixation system that includes one or more anchors that are capable of mono-, uni-, and poly-axial positioning and allow substantial vertical travel between the distal attachment point in the bone and the proximal position of a stabilization element, and are capable of locking to avoid further vertical travel after the system implantation is completed. Such an anchor would enable simplified attachment of adjacent anchors to a stabilization element by reducing the extent of height variability of adjacent anchors, thereby avoiding many of the challenges faced in the surgical setting.

SUMMARY

The present invention describes various exemplary systems and methods of installation of one or more anchors and stabilization elements that are adapted for height adjustability during spinal fixation surgery. The disclosure is directed in various embodiments, both described and contemplated, to assemblies, subassemblies and modular components and their methods of use and installation for achieving adjustable fixation and/or reduction of bones and bone fragments.

Provided in various embodiments is a length adjustable modular anchor system and methods of use thereof for engagement with a bone. In an exemplary embodiment, the length adjustable modular anchor system includes a length adjustable modular screw that includes a neck assembly and a shank.

In various embodiments, the disclosure provides a length adjustable modular screw that includes a neck assembly that has proximal and distal ends and includes an expander component and a collet component that are slidably engagable by insertion of the expander component in a through channel of the collet component along a common axis. The length adjustable modular screw also includes a shank suitable for insertion and retention within a bone, the shank including a threaded portion between its proximal and distal ends and a socket adapted to coaxially receive at least a portion of the distal end of the neck assembly. The length adjustable modular screw has a length that is selected by splaying at least a portion of the distal end of the engaged expander and neck components of the neck assembly within the socket of the shank. The length adjustable modular screw is one of monoaxial, uniaxial, and poly-axial.

BRIEF DESCRIPTION OF THE DRAWINGS

Various embodiments of the disclosed inventions will now be discussed with reference to the appended drawings. These drawings merely depict representative embodiments and are not limiting in scope.

TABLE of Reference Numerals

Figure 1:
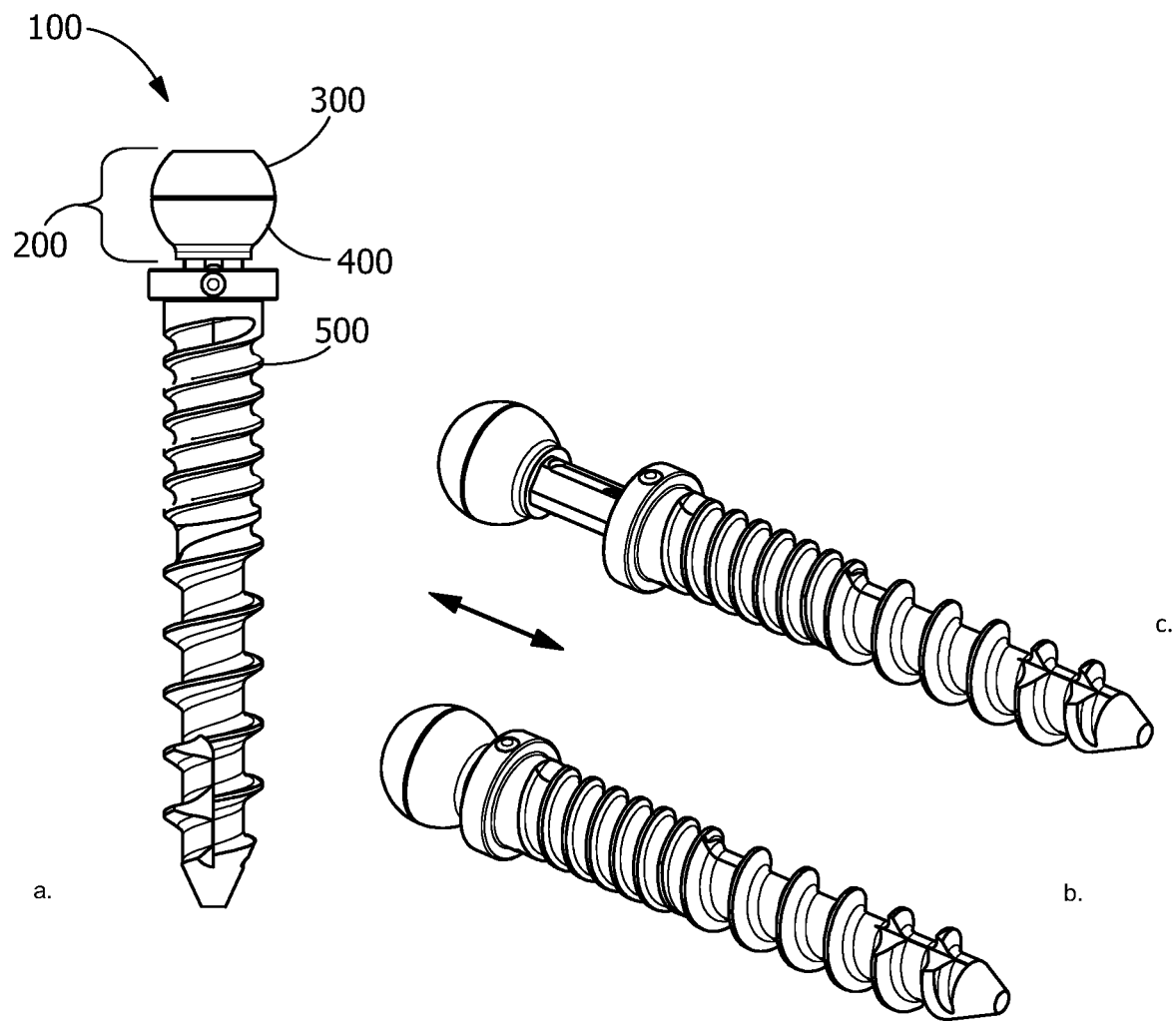
FIG. 1 shows a front plan view (a.) and alternate perspective views (b. and c.) of a length adjustable modular anchor system according to the disclosure.

| | |
|---|---|
| length adjustable modular anchor system 10 | through slot 452 |
| retaining housing 20 | interference enhancer 454 (e.g., groove/furrow/rib) |
| compression washer 30 (e.g., cap) | leg 456 |
| locking element 40 (e.g., set screw) | compression element 460 |
| rod (not shown) | complementary taper 462 |
| length adjustable modular screw 100 | shaped recess 470 |
| neck assembly 200 | recess proximal stop 472 |
| mated 220 | recess distal stop 474 |

TABLE-continued of Reference Numerals

| | |
|---|---|
| expander component 300 | outer surface 480 |
| head 310 (hemispherical) | chamfered corners 482 |
| foot 320 | collet cross sectional shape |
| foot cross sectional shape 322 | 490 (e.g., square) |
| pin 330 | shank 500 |
| taper 332 | threaded portion 510 |
| extension 334 | proximal end 520 |
| circumferential flange 340 | proximal aperture 522 |
| flange generally planar surface 345 | proximal thread zone 524 |
| flange taper 347 | distal end 530 |
| detent region 350 | distal tip 532 |
| drive recess 360 (hex) | distal thread zone 534 |
| pin 330 | socket 540 |
| cross sectional shape | socket cross sectional shape |
| 370 (e.g., sq/cyl) | 542 (e.g., sq/cyl) |
| collet component 400 | chamfered sidewall 544 |
| proximal end 410 | wall 550 |
| distal end 420 | wall aperture 560, 560' |
| through channel 430 | protuberance 570, 570' |
| inner wall 431 | floor 580 |
| inner wall cross sectional shape 432 (cylindrical) | floor taper 582 |
| seat 440 (hemispherical) | diameter 590 (e.g., straight, tapered, step down) |
| seat recess 441 | major diameter 592 |
| seat recess cross sectional shape 442 (e.g., sq/cyl) | minor diameter 594 |
| collet 450 | cannula 596 |
| | flange 598 |

DETAILED DESCRIPTION

This Detailed Description describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

The general inventive concepts will now be described with occasional reference to the exemplary embodiments of the invention. This general inventive concept may, however, be embodied in different forms and should not be construed as limited to the embodiments set forth herein. Rather, these embodiments are provided so that this disclosure will be thorough and complete, and will fully convey the scope of the inventive concepts to those skilled in the art.

Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts. As used in this detailed description and the appended claims, the singular forms "a," "an," and "the" are intended to include the plural forms as well, unless the context clearly indicates otherwise.

The term "proximal" as used in connection with any object refers to the portion of the object that is closest to the operator of the object (or some other stated reference point), and the term "distal" refers to the portion of the object that is farthest from the operator of the object (or some other stated reference point). A "clinical subject" refers to a human or other animal who is the subject of treatment with a bone fixation or reduction device in accordance with the disclosure. With respect to any references herein that may be made relative to a clinical subject, the term "cephalad" indicates a direction toward the head of the clinical subject, and the term "caudad" indicates a direction toward the feet of the clinical subject. The term "posterior" indicates a direction toward the back of the clinical subject, the term "anterior" indicates a direction toward the front of the clinical subject, and the term "lateral" indicates a direction toward a side of the clinical subject.

The term "height" as used specifically herein pertains to references to the spine of a clinical subject and refers to the relative position of one or both of vertebrae and anchors along adjacent portions of the spine. Likewise, the terms "vertical" and "vertical adjustment" relate to the relative height variations and adjustments thereof with respect to one or both of vertebrae and anchors along adjacent portions or the length of the spine in the context of a clinical subject in a prone position wherein a length adjustment to an anchor would be in a vertical dimension from anterior to posterior. These descriptors are not intended to be limiting with respect to embodiments of the modular adjustable assemblies, subassemblies and components according to the instant invention that are useful outside of the spine and may more generically be substituted with alternate descriptors including "length" and "length adjustment" where orientation of the clinical subject or body part and bones and implants vary.

As used herein in the described and illustrated embodiments, the term anchor typically refers to the screw component of an anchor assembly or subassembly, and the term anchor assembly refers to the screw component together with attachment features, such as a retaining housing (a conventional tulip head) or other type of attachment device, and one or more of compression washers and set screws, and optionally additional fixation components.

Subassemblies also refer to the modular components of the screw, such as, for example, the shank and head portions and subassemblies of these. More generically, anchor components, subassemblies and assemblies can be adapted to include features suitable for use with any bones in a clinical subject, wherein the modular and adjustable features are as described and claimed herein.

Unless otherwise indicated, all numbers expressing quantities of materials, properties such as length, diameter, and so forth as used in the specification and claims are to be understood as being modified in all instances by the term "about." Accordingly, unless otherwise indicated, the numerical properties set forth in the specification and claims are approximations that may vary depending on the suitable properties sought to be obtained in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

Referring now to the drawings, an embodiment of a modular and length adjustable modular anchor system 10 for securing a bone stabilization element, such as a spinal stabilization rod, to a bone is depicted in FIG. 1-FIG. 6. As further described herein, the length adjustable modular anchor system 10 includes a length adjustable modular screw 100 which can be varied in length.

Figure 6:
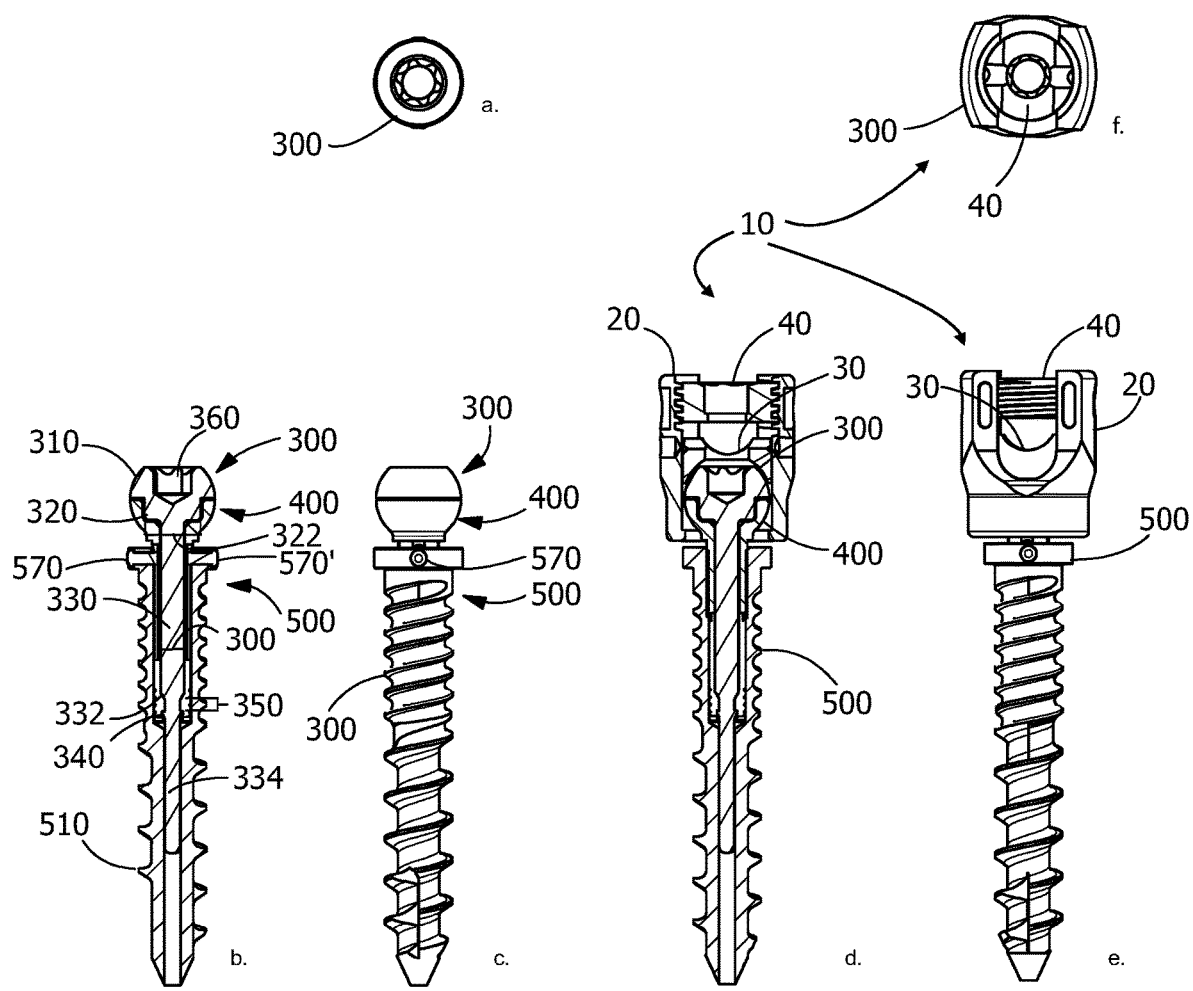
FIG. 6 shows on the top a top plan view (a.), and on the bottom side plan (b.) and cross sectional (c.) views of the length adjustable modular anchor system 10 shown in FIG. 1, and a top plan view (f.), side plan (d.) and cross sectional (e.) views of an alternate embodiment of a length adjustable modular anchor system 10 that includes a retaining housing 20, a compression washer 30 and a locking element 40 according to the disclosure.
Figure 7:
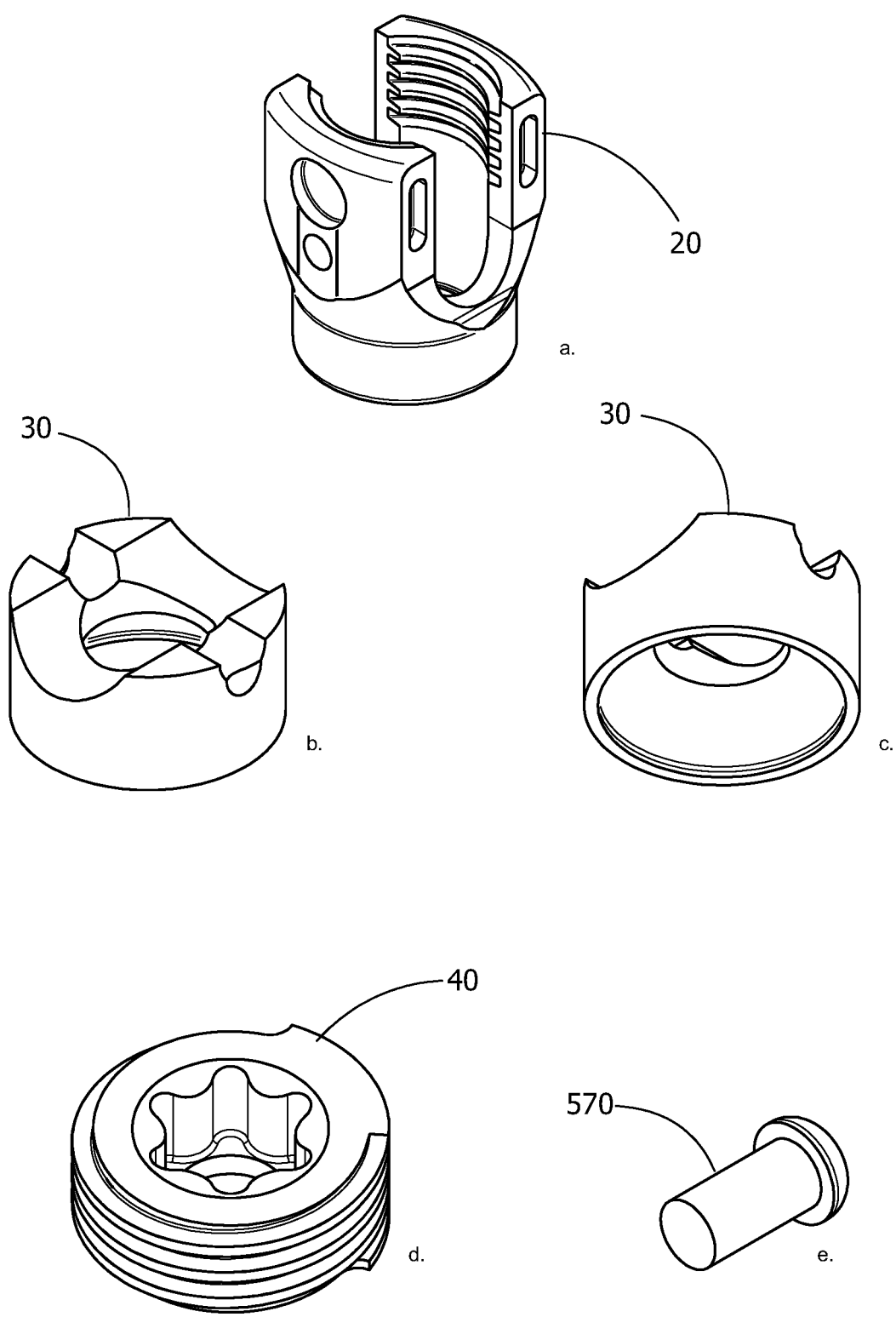
FIG. 7 shows each, individually in alternate views, the retaining housing 20 (a.), a compression washer 30 (top perspective, b., and bottom perspective, c.), locking element 40 (d.), and protuberance 570 (e.).

In accordance with the depicted embodiments, the length adjustable modular screw 100 is assembled to provide a construct that resembles a convention screw that includes a head 310 portion including at a proximal end 410 a hemispherical screw head and a separate threaded shank 500 portion including at a distal end a threaded shank 500. In accordance with the disclosure, the length adjustable modular screw 100 components are adapted for interconnection along a common elongate axis and capable of vertical displacement to achieve fixed or variable length when implanted in a bone. In conventional pedicle screw anchors, pressure from the rod locked into the retaining housing 20 (tulip head) by a threaded nut results in displacement of the compression washer 30 within the tulip head 20 and compression on the head of the screw thereby transferring compressive force onto the screw, fixing it into place within the tulip head 20 and preventing any axial rotation (for uni- and poly-axial assemblies). FIG. 6 provides an example of such a system that includes an embodiment of a length adjustable modular screw 100 according to the disclosure. In use, the compressive force employed to lock a rod to a conventional screw also serves to lock the length adjustable modular screw 100 embodiments according to this disclosure, thereby fixing the vertical position selected by the surgeon.

Length Adjustable Modular Anchor System

Figure 2:
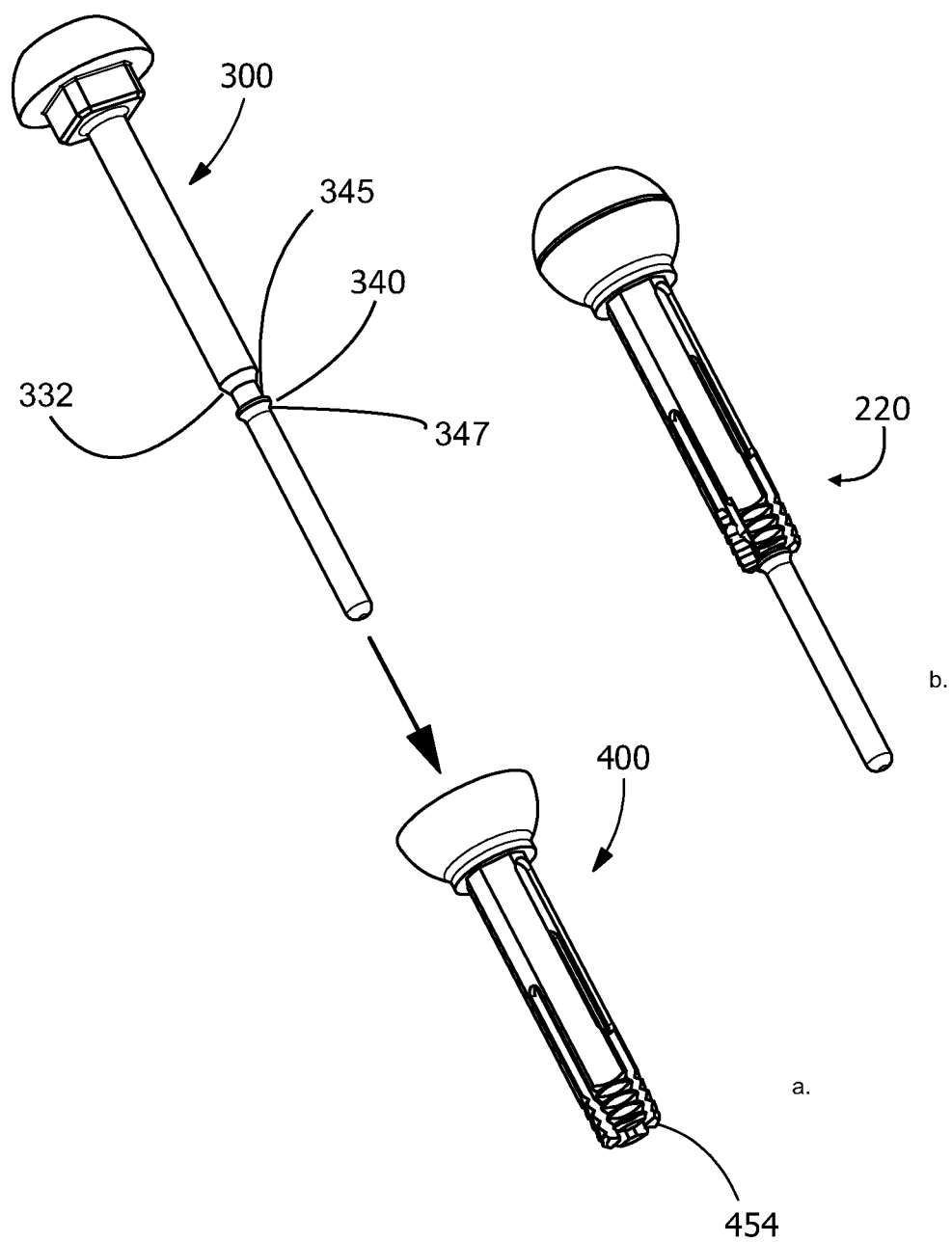
FIG. 2 shows exploded (a.) and assembled (b.) perspective views of the neck assembly of the length adjustable modular anchor system shown in FIG. 1.

Provided in alternate embodiments is a length adjustable modular anchor system 10 for engagement with a bone. In one embodiment, as shown in FIG. 1, the length adjustable modular anchor system 10 includes a length adjustable modular screw 100 that includes a neck assembly 200 and a shank 500. Referring now to FIG. 2, the neck assembly 200 includes an expander component 300 and a collet component 400. As assembled, a portion of the expander component 300 is insertable within a through channel 430 in the collet component 400 along a common axis, as shown in FIG. 2. The collet component 400 through channel 430 originates within the seat 440 and extends through the distal end 420 of the collet 450. When engaged, the head 310 of the expander component 300 contacts the seat of the collet component 400 and the pin 330 is passed through the through channel 430. In some embodiments, as depicted in the drawings, the expander component pin 330 includes an extension 334 that extends beyond the distal end 420 of the collet 450. In other embodiments, the expander component pin 330 may lack such an extension 334 and thus, the pin 330 may not extend beyond the distal end 420 of the collet 450.

The expander component 300 and the collet component 400 are engagable in each of open, mated and compressed configurations. In the open configuration, the expander component 300 and the collet component 400 are engaged without the head 310 contacting the seat 440 and the pin 330 of the expander component 300 is coaxially engaged with and only partially inserted in the through channel 430 of the collet component 400 and the expander and collet components 300, 400 are freely movable along the common axis.

Figure 3:
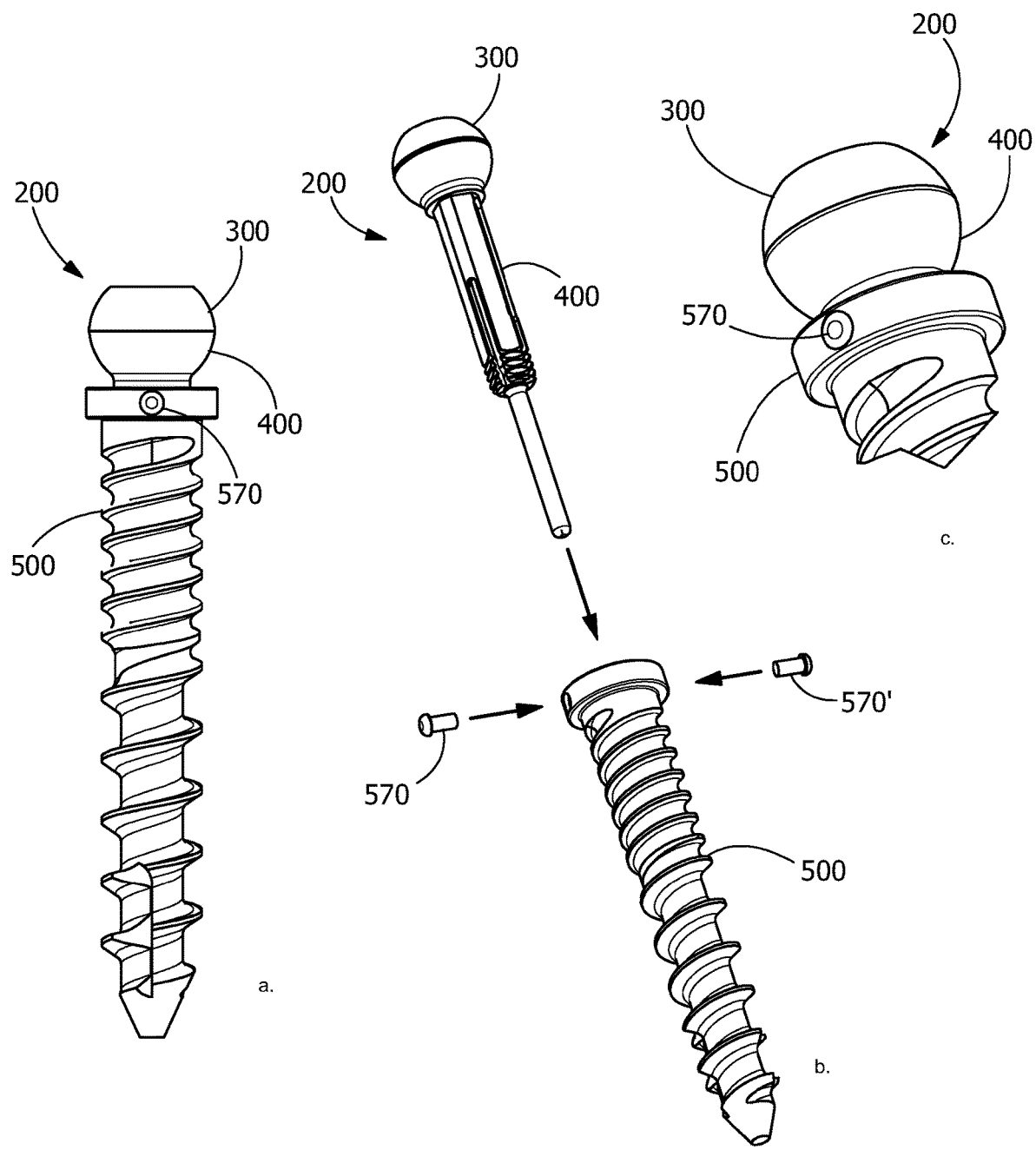
FIG. 3 shows a front plan view (a.), an exploded perspective view (b.) and a close up perspective (c.) view of the length adjustable modular anchor system shown in FIG. 1.

In the mated configuration, as shown in FIG. 3 (center image), the head 310 is contacting the seat 440 and the head 310 of the expander component 300 and the seat 440 of the collet component 400 are mated but not compressed, and the pin 330 of the expander component 300 is fully inserted in the through channel 430 of the collet component 400. In each of the open and the mated configurations, the collet 450 is not splayed. In the compressed configuration, the expander component 300 and the collet component 400 are mated and the head 310 and the seat 440 are contacted and in compression, and the collet 450 is splayed such that it has an overall greater diameter 590 than in its non-splayed configuration. Each of the expander and collet components 300, 400 include cooperating features that are compressible together to splay the collet 450.

Figure 4:
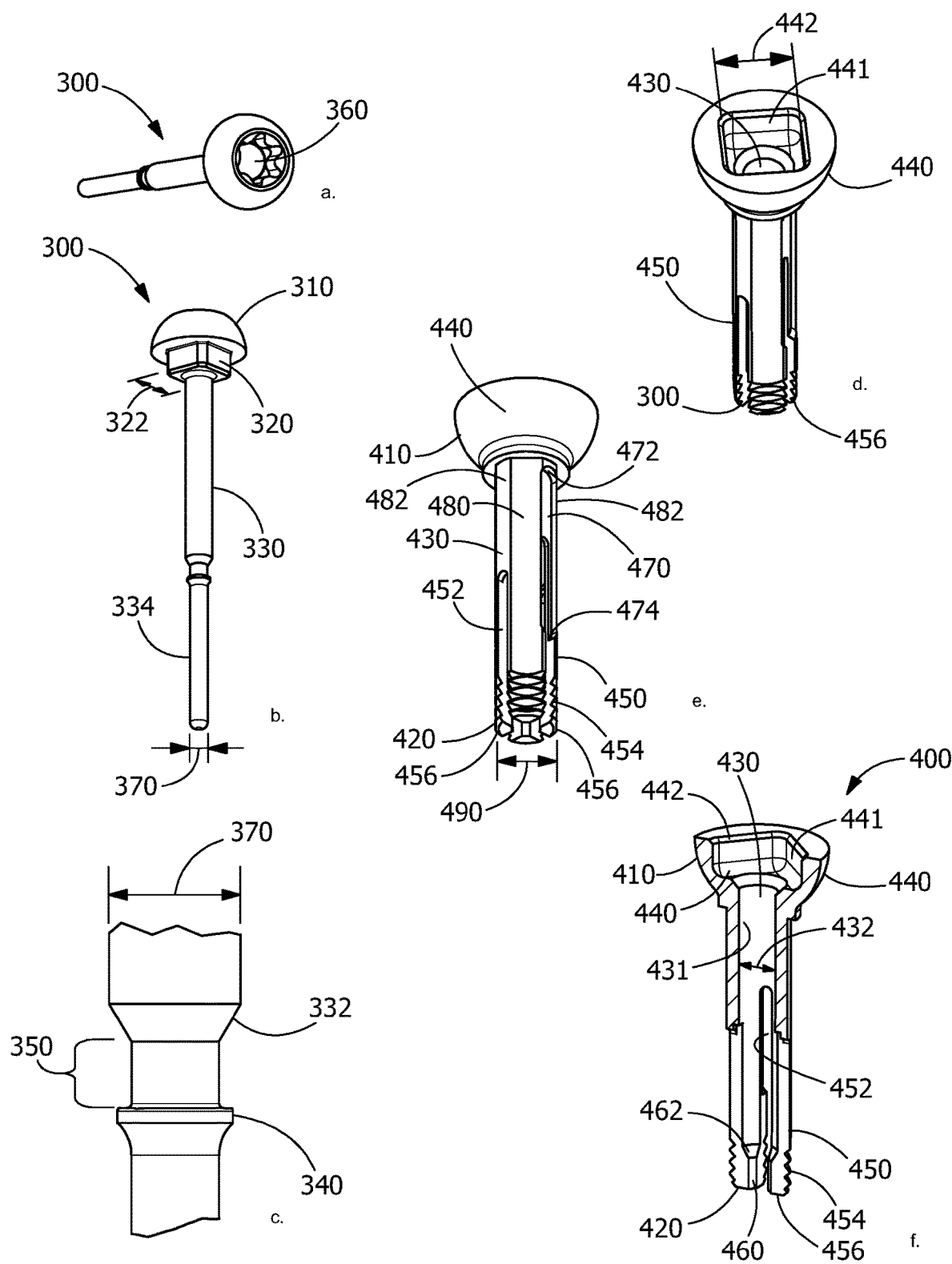
FIG. 4 shows on the left alternate top perspective (a.), side plan (b.), and partial close up side plan (c.) views of an expander component of the neck assembly shown in FIG. 2, and on the right alternate top perspective (d.), bottom perspective (e.), and side cross sectional (f.) views of a collet component of the neck assembly shown in FIG. 2.

Referring now to FIG. 4, left, the expander component 300 includes a head 310 at a proximal end and a pin 330 that extends from the head 310 at a distal end. Referring again to FIG. 4, right, the collet component 400 includes at a proximal end 410 a seat 440 that is matable with the head 310 of the expander component 300, and at a distal end 420 a collet 450 that extends from the seat 440. In some embodiments, each of the head 310 of the expander component 300 and the seat 440 of the collet component 400 are generally hemispherical in shape and mated 220 to form a generally spherical head 310, the mated 220 pin 330 and collet 450 features forming a generally rod-shaped extension from the sphere. Of course, it will be appreciated that in some embodiments, the head 310 and seat 440 features may be other than hemispherical. As depicted, the expander component 300 has a head 310 that is generally hemispherical and includes a flat at its apex that includes a drive recess 360 for engaging a driver. Any suitable shaped drive recess 360 may be employed for engagement with any of a variety of drivers.

As shown in the drawings, in some embodiments the head 310 of the expander component 300 includes a foot 320 having a generally square cross sectional shape, and the seat 440 of the collet component 400 includes a complementary seat recess 441 having a generally square cross sectional shape for receiving the foot 320 of the extender component 300.

In the various embodiments, the collet 450 includes at least one through slot 452 oriented parallel to the common axis and along at least a portion of the collet 450 through the distal end 420. And in some embodiments the collet 450 includes a plurality of through slots 452 arranged circumferentially around the collet 450 and extending along at least a portion of the length of the collet 450 and through the distal end 420. As shown in the drawings, for example FIG. 4, the collet 450 includes four through slots 452. In the depicted embodiment, the collet 450 has a generally square cross sectional shape 490, and each of the through slots 452 are arranged, respectively, on a side of the collet 450 to form four legs. As depicted, the collet 450 has chamfered corners 482 and generally planar sides on its outer surface. And the collet 450 includes on its outer surface at its distal end 420 an array of interference enhancers 454. As shown, the interference enhancers 454 include a knurled texture. In other embodiments, the feature may include other textural elements, or may include one or more furrows, divots or ridges. The interference enhancers 454 may enhance the contact with the wall 550 of the socket 540 within the shank 500 when the collet 450 is splayed. And the interference enhancers 454 may also enhance the flexibility of the shank 500 for splaying. It will be appreciated that in some embodiments the collet 450 lacks such interference enhancers 454. And as shown in the depicted embodiment, the collet 450 includes at its distal end 420 on each leg 456 and within the through channel 430 a compression element 460 that is generally block shaped with a proximally oriented taper or angle.

It will be appreciated that a variety of conventional features of collets 450 are known in the art and may be selected to facilitate locking and compression and/or frictional engagement between a collet 450 and engaged anchor components. In some instances, variations in the thickness of walls 550 of one or more components can be employed to achieve compressive engagement. In other examples, collet 450 features may include tapers along the length of engaging components. It will be understood that the features described herein are intended to be non-limiting and other features of collets 450 known in the art may be used to achieve the inventive modular and adjustable anchors in accordance with the invention.

In some embodiments, at least one of the expander component 300 and the collet component 400 includes a locking feature that is engagable when the head 310 of the expander component 300 and the seat 440 of the collet component 400 are mated 220. In some such embodiments, as is shown, for example in FIG. 2, the locking feature includes a circumferential flange 340 on the pin 330 of the expander component 300 that interferes with the distal end 420 of the collet 450 when the expander and collet components 300, 400 are in the mated 220 arrangement to limit displacement of the expander component 300. As shown in the drawings, the circumferential flange 340 is located at a position that is between the proximal and distal ends 410, 420 and includes a generally planar surface 345 on a proximal edge which abuts a taper 347 that is angled toward the common axis from proximal to distal to form a generally conical taper shape. And as shown, the pin 330 has a diameter at its proximal end 410 that is greater than the diameter at its distal end 420.

In some embodiments, the pin 330 of the expander component 300 also includes a detent region 350, which is shown in FIG. 2. As depicted, the detent region 350 has a diameter that is approximately the same as the diameter of the pin 330 at the distal end 420. And as depicted, the detent region 350 is abutted at its proximal end by a taper 332 that is angled toward the common axis from proximal to distal to form a generally conical shape and abuts at its distal end the generally planar surface 345 of the circumferential flange 340. Referring again to FIG. 4, the collet component 400 includes at least one compression element 460 within the collet 450 through channel 430 for contacting the taper 332 of the pin 330.

As shown in the drawings, for example in FIG. 2, the at least one compression element 460 of the collet 450 is engagable within the detent region 350 of the pin 330 of the expander component 300 when the expander and collet components 300, 400 are mated 220. In various embodiments, the compression element 460 extends into the collet 450 through channel 430, and has a shape that is one of angled, radiused and squared. In various embodiments, the compression element 460 may be formed continuously and interrupted only by the through slots 452, and may be dome shaped, may have planer circumferential flange 340 shape, may include one or more conical or beveled edges, and may be wedge shaped. And there may be more than one compression element 460 arranged along the length of the through channel 430.

Referring again to the drawings, for example FIG. 4, the pin 330 has a cross sectional shape 370 that is generally cylindrical and the through channel 430 of the collet component 400 has an inner wall 431 with an inner wall cross sectional shape 432 that is cylindrical. It will be appreciated that in other embodiments, each of the pin 330 cross sectional shape 370 and the inner wall cross sectional shape 432 may be other than cylindrical.

It will be appreciated that in other embodiments, the expander component 300 and the collet component 400 may include features that engage to mate and compress that are located at positions other than as shown in the drawings. For example, one or more of the circumferential flange 340 and the detent region 350 and the taper 332 on the pin 330 may be positioned more proximally or more distally, and the pin 330 may not include an extension beyond one or more of the circumferential flange 340 and the detent region 350 and the taper 332. Likewise, one or more of compression elements 460 may be positioned more proximally or more distally within the through channel 430 of the collet component 400.

As shown in the drawings, the expander component 300 pin 330 includes a conical taper 332 between the detent region 350 and a proximal portion of the pin 330, wherein the one or more compression elements 460 of the collet 450 comprises a complementary taper 462, which complementary taper 462, when pressed against the detent region 350 proximal taper 332 of the pin 330, splays the collet 450.

Figure 5:
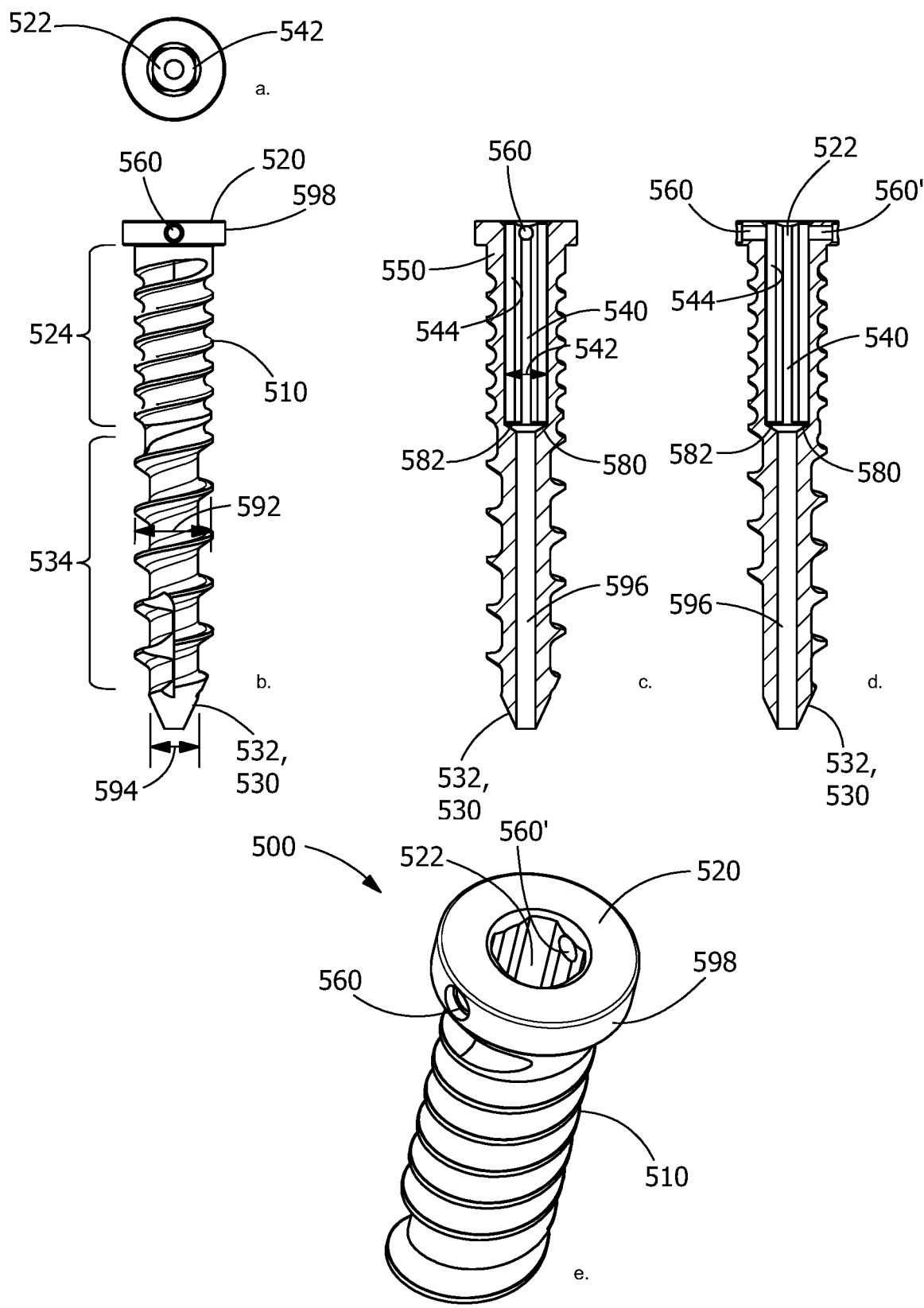
FIG. 5 shows an alternate side plan (b.), top, (a.) perspective (e.), and alternate side cross sectional (c. and d.) views of a shank component of the length adjustable modular anchor system 10 shown in FIG. 1.

Referring now to FIG. 1, FIG. 3, and FIG. 5, the length adjustable modular anchor system 10 also includes a shank 500 that includes a threaded portion 510 between proximal and distal ends 520, 530. As shown, the shank 500 includes at its distal end 530 a distal tip 532 that may be bulleted (not shown) and is suitable for penetrating bone. The shank 500 includes at its proximal end 520 an aperture that is in communication with a socket 540. The socket 540 extends within the shank 500 along a length from the proximal end 520 toward the distal end 530 and is adapted for receiving at least a portion of the collet 450 of the neck assembly 200. When the length adjustable modular anchor system 10 is assembled, the neck assembly 200 is adjustably engagable within the shank 500 to achieve variable length of the length adjustable modular screw 100.

In the various embodiments, the threaded portion 510 of the shank 500 may be continuous from the proximal to the distal ends 520, 530, or there may be a gap at either end that lacks threading, or a gap along the length that lacks threading. In the various embodiments, the shank 500 includes at least a major and a minor diameter 592, 594, the minor diameter 594 defined by the outer surface of the shank 500 wall 550 excluding the threads, and the major diameter 592 defined by the threads. In some embodiments, one or both of the major and minor diameters 592, 594 may be straight or may be tapered. In some embodiments, there may be a step down from proximal toward distal such that there may be more than one major diameter 592 and/or more than one minor diameter 594. In some embodiments, at least a portion of the length of the shank 500 may taper from proximal to distal either continuously or may taper in a stepped down manner. In some embodiments, the threading may vary to provide a proximal thread zone 524 that is different from a distal thread zone 534.

Referring again to the drawings, the depicted collet has a cross sectional shape 490 that is generally square and the socket 540 of the shank 500 has a socket cross sectional shape 542 that is square, each of the collet 450 and the socket 540 including chamfered corners 482 and chamfered sidewalls 544, respectively. It will be appreciated that in other embodiments, each of the collet cross sectional shape 490 and the socket cross sectional shape 542 may be other than square and may be cylindrical.

As shown, for example in FIG. 3, the shank 500 includes at least one, and as depicted, includes two wall apertures 560, 560' that are adapted for receiving a protuberance 570 through each for engagement with the neck assembly 200, as described further below. It will be appreciated that in some embodiments, protuberance 570 may be integrated with the shank 500. And while the drawings show the pin 330 insertable in an aperture 560, 560' through a flange 598 on the shank 500, in some embodiments, the shank 500 may lack a flange 598.

In accordance with some embodiments, the length adjustable modular screw 100 further includes at least one locking feature on at least one of the neck assembly 200 and the shank 500 that engages to retain the neck assembly 200 within the shank socket 540. Referring now to FIG. 3 and FIG. 4, in some embodiments, the locking feature includes a shaped recess 470 along at least a portion of the length of the collet component 400 and a complementary protuberance 570 situated at the proximal end 520 of the shank 500. The protuberance 570 extends into the shank socket 540 and is engagable with the shaped recess 470 of the collet component 400. The locking feature prevents pull out of the neck assembly 200 from the shank socket 540. The locking feature also limits rotational motion of the neck assembly 200 within the socket 540. As shown, the shaped recess 470 has a generally elliptical shape and is elongate from the proximal 410 and towards the distal end 420 of the collet component 400. The shaped recess 470 includes proximal and distal stops 472, 474. It will be appreciated that other shapes for the shaped recess 470 may be employed, and the shaped recess 470 may have a longer or shorter length along the collet 450.

Other features of the neck assembly 200 engage with the shank 500 to further stabilize the engagement. Referring again to the drawings, the expander component pin 330 includes an extension 334 at its distal end, and the shank socket 540 includes a floor 580 and cannula 596 extending from the floor 580 towards the distal end 530. The distal end 420 of the collet 450 contacts the floor 580 to limit the distal passage of the neck assembly 200 within the socket 540, and the cannula 596 is adapted to receive the expander component 300 extension which aids in stabilizing against off axis motion of the neck assembly 200 relative to the shank 500. In some embodiments, the length of each of the extension of the expander component 300 and the shaped recess 470 of the collet 450 are selected such that when the neck assembly 200 is displaced proximally to the limit of the distal stop 474, the extension is retained in the cannula 596 to maximize off axis stabilization together with restriction on axis pull out. As is shown in the drawings, the floor 580 of the shank 500 has a generally conical floor taper 582. In some embodiments, the floor 580 may have another shape, and may be planar, or have a spherical contour or another shape.

It will be appreciated that in alternate embodiments different or additional engagement features may be used that achieve the fixed engagement between subcomponents. Such engagement is useful to enable torsional engagement and actuation, such as with a driving tool, of one or more components while preventing other components from experiencing torsional force. Likewise, it is advantageous to employ engagement features that serve as stops to prevent disengagement of components by the application of shear force, such as pull out of axially aligned components.

Referring again to FIG. 6, an embodiment of a length adjustable modular anchor system 10 for engagement with a bone is shown. The length adjustable modular anchor system 10 includes a length adjustable modular screw 100 comprising a neck assembly 200 and a shank 500, a rod (not shown) and at least one retaining housing 20 and a locking element 40 for engaging and securing the length adjustable modular screw 100 and the surgical rod. Optionally, the length adjustable modular anchor system 10 also includes one or more compression washers 30 for engagement between the rod and a bone anchor. In use, one or more than one length adjustable modular anchor system 10 may be employed together with one or more conventional bone anchors, and additional components including surgical rods (or other stabilizing members, not shown), retaining housings 20, locking elements 40 and optional components such as compression washers 30. Arrays of anchors and rods may be used for example to stabilize adjacent vertebral bodies which may include placement of up to four or more anchors, two each within pedicles of adjacent vertebral bodies and engagement of a spinal rod to each of the pair of adjacent anchors to confer stabilization along the length of the spine.

Also provided according to the disclosure is a surgical method for installing a bone anchor system for spinal fixation. According to the method, the steps include in some embodiments selecting each of two or more bone anchors, at least one of which bone anchors is a length adjustable modular anchor system 10 that includes a neck assembly 200 and a shank 500, as described herein above, and at least one spinal rod defining a longitudinal axis, and two or more retaining housings 20 for engaging and securing a bone anchor and a surgical rod, and two or more locking elements 40 for securing a rod to a bone anchor, and optionally, one or more compression washers 30 for engagement between a rod and a bone anchor. Further according to the method, the steps include, either before or after seating the neck assembly 200 in a retaining housing 20, assembling a length adjustable modular screw 100 system.

The steps for assembling a length adjustable modular screw 100 system include first engaging the expander and collet components 300, 400 of the neck assembly 200 into one of open and mated 220 engagement, and inserting the neck assembly 200 into the shank 500 socket 540, then contacting the distal tip 532 of the shank 500 with a bone. Thereafter, using a suitable driver, engaging the drive recess 360 of the neck assembly 200 to compress the expander and collet components 300, 400 and splay the collet 450. Thereafter, under continued compression, driving the threaded portion 510 of the shank 500 into a bone. Once the shank 500 is inserted to the desired depth in bone, the steps include releasing the drive compression on the drive recess 360 of the neck assembly 200 to thereby relieve the collet 450 from being splayed and thereby allowing translation of the neck assembly 200 within the shank 500.

Thereafter, either before or after provisionally securing a surgical rod into the retaining housing 20, the vertical height (length) of the length adjustable modular anchor system 10 may be adjusted by sliding the neck assembly 200 along the common axis within the socket 540 of the shank 500. Once the desired length and vertical height relative to adjacent anatomy and/or other anchors or implants is selected, the method includes tightening the fixation element within the retaining housing 20 to compress the rod against the neck assembly 200 and to drive the expander component 300 and the collet component 400 into compressed engagement to splay the collet 450 within the socket 540 of the shank 500.

In some embodiments of the surgical method, the length adjustable modular anchor system 10 is fully assembled prior to engagement of the threaded portion 510 of the shank 500 with bone. In yet other embodiments, the length adjustable modular anchor system 10 is provided pre-assembled. And in yet other embodiments, at least the neck assembly 200 of the length adjustable modular anchor system 10 is provided pre-assembled with a retaining housing 20.

In some embodiments, the length adjustable modular screw 100 can be adjusted within a displacement range between zero mm to 20 mm, and more particularly 0 mm to 10 mm, including fractional increments therein, including 0.1, 0.2, 0.3, 0.4, 0.5, 1.0, 1.5, 2.0, and 2.5 up to and through 20.0 mm. Of course, other increments and ranges of travel are possible, and implementation thereof is well within the skill in the art.

It will be appreciated that in each of the various embodiments according to the invention, more than one length adjustable modular screw may be provided that are of varying lengths and therefore allow for an expanded range of length adaptability. Whether the length adjustable modular screw components are of fixed length or offered in ranges of lengths, such possible embodiments are particularly advantageous in that they provide options in some embodiments for providing preassembled bottom and top loading anchor assemblies, as well as anchor assemblies and subassemblies that may be assembled partially by the manufacturer or partially or completely by the surgeon, providing a range of options for achieving maximal flexibility in the surgical setting.

As described herein in accordance with the depicted embodiments, the components of the length adjustable modular screw 100 assembly that achieve locking of the length adjustable modular screw 100 to a rod can also actuate the collet 450 locking mechanism for fixing the neck assembly 200 of the length adjustable modular anchor system 10 to the shank 500 and optionally fixing the vertical position of the length adjustable modular screw 100 relative to the vertebra and the fixation system elements. Of course, in other embodiments, the means of achieving locking may be other than compression by the rod, and in yet other embodiments the locking means may be the same but the specific elements, such as the locking element 40, rod and compression washer 30, may be varied.

Reference is made herein to fixation systems that include in the depicted embodiments anchors in the form of vertebral pedicle screws, and stabilization elements in the form of one or more surgical rods. It will be appreciated by those skilled in the art that the spine is but one example of a bone or bone system that may be the object of surgical correction, and thus, pedicle screws and rods are mere examples of the bone anchor, and vertebral stabilization system components contemplated herein. In other examples, anchors may be screws for engagement with a tether or other tensioning means, or with one or more plates or rods or combinations of these. And anchors and systems described herein may be suitable for other bones and bone systems in the body. Moreover, it will be appreciated that the mechanisms for adjustment of anchor length can be adapted for use with other anchor and fixation and stabilization elements used in orthopedic applications in the spine or in other parts of the body.

In one example, spinal rods may be made adjustable according to the features disclosed herein to enable tuned adjustment of rod length at the time of implantation or subsequently as spinal healing and or adjustment takes place, such as for adjustment of rod length in connection with scoliosis treatment. In yet other examples, adjustable anchors may be employed in the reduction or fixation of other bones, such as bones of the hand, or of the foot or in other locations where adjustment of the length of an anchor or other fixation element is desirable. One such example would be incorporation of adjustability features disclosed herein in dual threaded headless screws or screws, rods or pins with other head and threading configurations that are used for interconnecting and reducing fractured bone fragments or adjacent bones. Such anchors adapted according to the instant disclosure would enable tuned adjustment of implant length to accommodate anatomical variations in a clinical subject and achieve optimized anchor placement.

The invention is directed in various aspects to a system including assemblies and subassemblies, components including anchors and anchor components adapted for attachment to a bony structure of a clinical subject. In an exemplary embodiment wherein the use is in connection with fixation of the spine, wherein one, two or more such anchors in the form of screws are affixed to bones, for example, vertebral structures such as the pedicle, and each anchor is connected to a stabilizer such as a surgical rod that is inserted between the anchors. The anchors are novel in many respects owing to their modular nature and thus the options to provide the anchors in modular, sub-assembled and assembled forms provide a broad array of choices for the surgeon in devising the optimal surgical fixation plan.

In use by a surgeon, installation of the inventive components of the exemplary bone anchor system for spinal fixation described above includes: selecting two or more bone anchor assemblies or subassemblies, including assemblies and subassemblies selected from pre-assembled and top and bottom loading forms, wherein at least one anchor assembly includes an length adjustable modular screw; selecting a stabilization element; using a suitable driver to drive each of two or more anchors or anchor subassemblies into fixed engagement with corresponding vertebrae, wherein at least one anchor or anchor subassembly includes or is adapted to engage with modular components that allow length adjustability, including translation along the vertical axis of the anchor, so as to enable selection of the anchor length by the surgeon; engaging a proximal portion of the modular adjustable anchor, such modular portion selected from a pre-assembled or modular screw head and engagement seat, to provide a means to introduce the stabilization element into engagement with the anchor; optionally incrementally adjusting the length of the anchor so as to achieve engagement of the stabilization element in the anchor; sliding the stabilization element into place within the anchor; introducing a fixation element to at least temporarily fix the stabilization element within the anchor; optionally, adjusting at least the vertical position of the anchor to optimize its height orientation relative to the stabilization element and adjacent anchors; tightening the fixation element to compress the stabilization element within the anchor assembly, thereby fixedly engaging the modular components of the anchor so as to lock the position of the anchor and also lock its engagement with the stabilization element. This process is repeated for each adjustable anchor in the system, and conventional methods are used with conventional anchors.

It will be appreciated by one of skill in the art that the length adjustable modular screw described herein may be employed with components of a conventional spinal stabilization system, and may be used on a single vertebra, or traversing two or more vertebra, and may be used in conjunction with fusion or non-fusion treatment of the spine. Of course, in various examples, the anchors may be employed in isolation or in systems that include two or more anchors, connectors and stabilization elements, and the anchors may be deployed other than along the spinal axis. Thus, in other examples of use, two or more anchors may be used to secure one or more stabilization elements that extend either laterally or from an anterior to posterior aspect to traverse a vertebral body, or that wrap around one or more vertebral bodies, or combinations of these. And of course it will be appreciated that in some examples the assemblies and subassemblies, components, including anchors and anchor components, may be used in bones of the body other than the spine, and as such may be used individually, as a plurality, or in combination with other devices, and combinations of these.

What is claimed:

1. A length adjustable modular screw comprising: a neck assembly that includes an expander component and a collet component, the neck assembly having proximal and distal ends, wherein the expander and collet components are slidably engagable by insertion of the expander component in a through channel of the collet component along a common axis, and a shank suitable for insertion and retention within a bone, the shank including a threaded portion between its proximal and distal ends and a socket adapted to coaxially receive at least a portion of the distal end of the neck assembly, wherein the length adjustable modular screw has a length that is selected by splaying at least a portion of the distal end of the engaged expander and collet components of the neck assembly within the socket of the shank.

2. The length adjustable modular screw according to claim 1, wherein the expander component of the neck assembly includes an extension that extends beyond the distal end of the collet component of the neck assembly.

3. The length adjustable modular screw according to claim 1, the expander component comprising an extension at its distal end, and the socket of the shank comprising a cannula extending towards the distal end, the cannula adapted to receive the expander component extension.

4. The length adjustable modular screw according to claim 1, wherein the expander and collet components are matable at their proximal ends when the expander component is inserted in the through channel of the collet component.

5. The length adjustable modular screw according to claim 3, wherein the neck assembly comprises a generally spherical head when the expander and collet components are mated.

6. The length adjustable modular screw according to claim 1, wherein the expander component comprises a head at its proximal end and the collet component comprises a seat at its proximal end, wherein the head and seat, when mated form a generally spherical head on the neck assembly.

7. The length adjustable modular screw according to claim 6, wherein each of the head and the seat are hemispherical.

8. The length adjustable modular screw according to claim 1, wherein the length adjustable modular screw is one of monoaxial, uniaxial, and poly-axial.

9. The length adjustable modular screw according to claim 1, wherein the neck assembly components are engageable from between an open arrangement and a compressed arrangement.

10. The length adjustable modular screw according to claim 9, wherein the neck assembly in the open arrangement provides free movement of the expander component within the collet component along the common axis.

11. The length adjustable modular screw according to claim 1, wherein the modular screw is engageable with a retaining housing that is configured for accepting a rod and a fixation screw.

12. The length adjustable modular screw according to claim 1, wherein an elongate component of the expander assembly comprises at least one through slot extending, or a plurality of circumferentially arranged through slots, extending along at least a portion of the length of its distal end.

13. The length adjustable modular screw according to claim 11, the one or plurality of through slots being disposed on the second elongate component.

14. A length adjustable modular screw comprising: a neck assembly that includes an expander component and a collet component, the neck assembly having proximal and distal ends, wherein the expander and collet components are slidably engagable by insertion of the expander component in a through channel of the collet component along a common axis, wherein the expander and collet components are matable at their proximal ends when the expander component is inserted in the through channel of the collet component, the expander component comprising a head at its proximal end and the collet component comprising a seat at its proximal end, wherein the head and seat, when mated form a generally spherical head on the neck assembly; and a shank suitable for insertion and retention within a bone, the shank including a threaded portion between proximal and distal ends and a socket adapted to coaxially receive at least a portion of the distal end of the neck assembly, wherein the length adjustable modular screw has a length that is selected by splaying at least a portion of the distal end of the engaged expander and collet components of the neck assembly within the socket of the shank.

\* \* \* \* \*